United States Patent
Audousset

(10) Patent No.: US 6,406,502 B1
(45) Date of Patent: Jun. 18, 2002

(54) COMPOSITIONS FOR THE OXIDATION DYEING OF KERATIN FIBRES AND DYEING PROCESS

(75) Inventor: Marie-Pascale Audousset, Asnieres (FR)

(73) Assignee: L'Oreal, Clichy Cedex (FR)

( * ) Notice: Subject to any disclaimer, the term of this patent is extended or adjusted under 35 U.S.C. 154(b) by 0 days.

(21) Appl. No.: 09/609,382

(22) Filed: Jul. 3, 2000

Related U.S. Application Data

(63) Continuation of application No. 08/896,671, filed on Jul. 18, 1997, now abandoned.

(30) Foreign Application Priority Data

Jul. 19, 1996 (FR) .............................. 96 09108

(51) Int. Cl.[7] ................................. A61K 7/13
(52) U.S. Cl. ...................... 8/405; 8/405; 8/406; 8/408; 8/411
(58) Field of Search ............................. 8/407, 408, 411, 8/405, 406

(56) References Cited

U.S. PATENT DOCUMENTS

| 4,330,292 A | * | 5/1982 | Bugaut et al. ................. 8/411 |
| 4,333,730 A | * | 6/1982 | Bugaut et al. ................. 8/407 |
| 5,567,421 A | * | 10/1996 | Cotteret et al. ............ 424/70.1 |
| 5,863,300 A | | 1/1999 | Audousset et al. ............ 8/411 |

FOREIGN PATENT DOCUMENTS

| EP | 0 591 059 | 4/1994 |
| EP | 0 605 320 | 7/1994 |
| EP | 0 662 317 | 7/1995 |
| EP | 0 667 143 | 8/1995 |
| EP | 0 722 713 | 7/1996 |
| FR | 2 687 308 | 8/1993 |
| FR | 2 687 399 | 8/1993 |
| WO | WO 9318739 | 9/1993 |

OTHER PUBLICATIONS

English Derwent Abtract of EP 0 662 317.
English Derwent Abtract of EP 0 667 143.
English Derwent Abtract of EP 0 591 059.
English Derwent Abtract of FR 2 687 399.
English Derwent Abtract of WO 93 18739.
English Derwent Abtract of FR 2 687 308
English Derwent Abtract of EP 0 605 320.
English Derwent Abtract of EP 0 722 713.

* cited by examiner

*Primary Examiner*—Mark Kopec
*Assistant Examiner*—Eisa B Elhilo
(74) *Attorney, Agent, or Firm*—Finnegan, Henderson, Farabow, Garrett & Dunner LLP

(57) ABSTRACT

A composition for the oxidation dyeing of keratin fibers, in particular of human keratin fibers such as the hair, preferably comprising 2-n-propyl-para-phenylenediamine, in combination with at least one meta-phenylenediamine, as well as to the dyeing process using this composition.

23 Claims, No Drawings

COMPOSITIONS FOR THE OXIDATION DYEING OF KERATIN FIBRES AND DYEING PROCESS

This is a continuation of application Ser. No. 08/896,671 filed Jul. 18, 1997, now abandoned which is incorporated herein by reference.

The invention relates to a composition for the oxidation dyeing of keratin fibres, in particular of human keratin fibres such as the hair, comprising 2-n-propyl-para-phenylenediamine, in combination with at least one meta-phenylenediamine, as well as to the dyeing process using this composition.

It is known to dye keratin fibres, and in particular human hair, with dye compositions containing oxidation dye precursors, in particular ortho or para-phenylenediamines, or ortho or para-aminophenols, which are generally referred to as oxidation bases. The oxidation dye precursors, or oxidation bases, are colourless or weakly coloured compounds which, when combined with oxidizing products, may give rise to coloured compounds and dyes by a process of oxidative condensation.

It is also known that the shades obtained with oxidation bases may be varied by combining them with couplers or coloration modifiers, it being possible for the latter to be chosen in particular from aromatic meta-diamines, meta-aminophenols and meta-diphenols.

The variety of molecules used as oxidation bases and couplers makes it possible to obtain a wide range of colours.

The so-called "permanent" coloration obtained by means of these oxidation dyes seeks to satisfy a certain number of requirements. Thus, it is desired to have no toxicological drawbacks and to allow shades of the desired intensity to be obtained and to have good staying power with respect to external agents (light, inclement weather, washing, permanent-waving, perspiration and rubbing).

It is also desired that the dyes allow white hairs to be covered and, lastly, to be as unselective as possible, that is to say to allow the smallest possible differences in coloration to be produced over the entire length of the same keratin fibre, which may indeed be differently sensitized (i.e. damaged) between its tip and its root.

Compositions for the oxidation dyeing of keratin fibres, containing at least one meta-phenylenediamine derivative as coupler, in combination with at least one oxidation dye precursor of para-phenylenediamine type or derivatives, have already been proposed. However, the colorations obtained with these compositions are not entirely satisfactory, in particular regarding the staying power of these colorations with respect to the various attacking factors to which the hair may be subjected, and in particular shampoos.

The present invention is aimed at proposing novel compositions for the oxidation dyeing of keratin fibres, and in particular of human keratin fibres such as the hair, which have very good dyeing properties.

Thus, the inventor has just discovered that it is possible to obtain novel dyes of particularly good staying power, which lead to intense colorations, by combining:
- at least one oxidation base selected from 2-n-propyl-para-phenylenediamine and acid addition salts thereof, and
- at least one coupler selected from meta-phenylenediamines of formula (I) defined below and acid addition salts thereof.

This discovery forms the basis of the present invention.

The first subject of the invention is thus a composition for the oxidation dyeing of keratin fibres, and in particular of human keratin fibres such as the hair, characterized in that it comprises, in a medium which is suitable for dyeing:
- at least one oxidation base selected from 2-n-propyl-para-phenylenediamine and acid addition salts thereof, and
- at least one coupler selected from meta-phenylenediamines of formula (I) below and acid addition salts thereof:

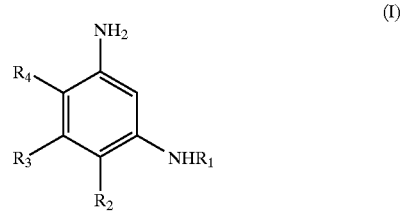

wherein:
- $R_1$ represents a hydrogen atom or a $C_1$–$C_4$ alkyl, $C_1$–$C_4$ monohydroxyalkyl or $C_2$–$C_4$ polyhydroxyalkyl radical;
- $R_2$ and $R_3$, which may be identical or different, represent a hydrogen atom or a $C_1$–$C_4$ alkyl, $C_1$–$C_4$ monohydroxyalkoxy or $C_2$–$C_4$ polyhydroxyalkoxy radical;
- $R_4$ represents a hydrogen atom or a $C_1$–$C_4$ alkoxy, $C_1$–$C_4$ aminoalkoxy, $C_1$–$C_4$ monohydroxyalkoxy or $C_2$–$C_4$ polyhydroxyalkoxy radical or a 2,4-diaminophenoxyalkoxy radical.

As demonstrated by the examples below, the colorations obtained with the above compositions are of good dyeing power and have excellent properties of staying power both with regard to atmospheric agents such as light and bad weather and with regard to perspiration and the various treatments to which the hair may be subjected (shampooing, permanent-waving). These properties are particularly noteworthy, especially regarding the staying power of the colorations obtained with respect to shampooing.

The subject of the invention is also a process for the oxidation dyeing of keratin fibres using this composition.

The addition salts with an acid which may be used within the context of the dye compositions of the invention may be chosen in particular from hydrochlorides, hydrobromides, sulphates and tartrates.

Among the meta-phenylenediamines of formula (I) above which may be mentioned more particularly are meta-phenylenediamine, 3,5-diamino-1-ethyl-2-methoxy-benzene, 3,5-diamino-2-methoxy-1-methylbenzene, 2,4-diamino-1-ethoxybenzene, 1,3-bis(2,4-diaminophenoxy) propane, bis(2,4-diaminophenoxy)methane, 1-(β-aminoethyloxy)-2,4-diaminobenzene, 2-amino-1-(β-hydroxyethyloxy)-4-methylaminobenzene, 2,4-diamino-1-ethoxy-5-methylbenzene, 2,4-diamino-5-(β-hydroxyethyloxy)-1-methylbenzene, 2,4-diamino-1-(β,γ-dihydroxypropyloxy)benzene, 2,4-diamino-1-(β-hydroxyethyloxy)benzene and 2-amino-4-N-(β-hydroxyethyl)amino-1-methoxybenzene, and the addition salts thereof with an acid.

The 2-n-propyl-para-phenylenediamine and/or the addition salt or salts of this compound with an acid preferably represent from 0.0005 to 10% by weight approximately relative to the total weight of the dye composition, and even more preferably from 0.05 to 7% by weight approximately.

The meta-phenylenediamine(s) of formula (I) in accordance with the invention preferably represent(s) from 0.0001 to 5% by weight approximately relative to the total weight of the dye composition, and even more preferably from 0.005 to 3% by weight approximately.

The appropriate medium for the dyeing (or the support) generally comprises water or a mixture of water and at least one organic solvent to solubilize the compounds which would not be sufficiently soluble in water. Organic solvents which may be mentioned, for example, are $C_1$–$C_4$ lower alkanols such as ethanol and isopropanol; glycerol; glycols and glycol ethers such as 2-butoxyethanol, propylene glycol, diethylene glycol monoethyl ether and monomethyl ether, and aromatic alcohols such as benzyl alcohol or phenoxyethanol, similar products and mixtures thereof.

The solvents may be present in proportions preferably approximately from 1 to 40% by weight relative to the total weight of the dye composition, and even more preferably approximately 5 to 30% by weight.

The pH of the dye composition as described above generally ranges approximately from 5 to 12. It may be adjusted to the desired value using acidifying or basifying agents usually used in the dyeing of keratin fibres.

Among the acidifying agents which may be mentioned, by way of example, are inorganic or organic acids such as hydrochloric acid, orthophosphoric acid, carboxylic acids such as tartaric acid, citric acid and lactic acid, and sulphonic acids.

Among the basifying agents which may be mentioned, by way of example, are aqueous ammonia, alkaline carbonates, alkanolamines such as mono-, di- and triethanolamines and derivatives thereof, sodium hydroxide, potassium hydroxide and the compounds of formula (II) below:

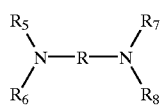

(II)

in which R is a propylene residue optionally substituted with a hydroxyl group or a $C_1$–$C_4$ alkyl radical; $R_5$, $R_6$, $R_7$ and $R_8$, which may be identical or different, represent a hydrogen atom or a $C_1$–$C_4$ alkyl or $C_1$–$C_4$ hydroxyalkyl radical.

The dye composition in accordance with the invention may also contain, in addition to the dyes defined above, other oxidation bases and/or other couplers and/or direct dyes, especially in order to modify the shades or to enrich them with glints.

The dye composition according to the invention may also include various adjuvants used conventionally in compositions for dyeing the hair, such as anionic, cationic, nonionic, amphoteric or zwifterionic surfactants or mixtures thereof, anionic, cationic, nonionic, amphoteric or zwitterionic polymers or mixtures thereof, inorganic or organic thickeners, antioxidants, penetration agents, sequestering agents, fragrances, buffers, dispersing agents, conditioners such as, for example, silicones, film-forming agents, preserving agents and opacifying agents.

Obviously, a person skilled in the art will take care to select this or these optional complementary compound(s) such that the advantageous properties intrinsically associated with the dye composition in accordance with the invention are not, or are substantially not, adversely affected by the addition or additions envisaged.

The dye composition according to the invention may be in various forms, such as in the form of liquids, creams, gels or any other form which is suitable for dyeing keratin fibres, and in particular human hair.

The subject of the invention is also a process for dyeing keratin fibres, and in particular human keratin fibres such as the hair, using the dye composition as defined above.

According to this process, the dye composition as defined above is applied to the fibres, the colour being developed at acidic, neutral or alkaline pH using an oxidizing agent which is added only at the time of use to the dye composition or which is present in an oxidizing composition that is applied simultaneously or sequentially in a separate manner.

According to a particularly preferred embodiment of the dyeing process according to the invention, the dye composition described above is mixed, at the time of use, with an oxidizing composition containing, in a medium which is suitable for dyeing, at least one oxidizing agent present in an amount which is sufficient to develop a coloration. The mixture obtained is then applied to the keratin fibres and is preferably left in place for 3 to 40 minutes approximately, more preferably 5 to 30 minutes approximately, after which the fibres are rinsed, washed with shampoo, rinsed again and dried.

The oxidizing agent present in the oxidizing composition as defined above may be chosen from the oxidizing agents conventionally used for the oxidation dyeing of keratin fibres, and among which mention may be made of hydrogen peroxide, urea peroxide, alkali metal bromates and persalts such as perborates and persulphates. Hydrogen peroxide is particularly preferred.

The pH of the oxidizing composition containing the oxidizing agent as defined above is such that, after mixing with the dye composition, the pH of the resulting composition applied to the keratin fibres preferably ranges approximately from 2 to 12 and even more preferably from 5 to 11. It is adjusted to the desired value using acidifying or basifying agents usually used in the dyeing of keratin fibres and as are defined above.

The oxidizing composition as defined above may also include various adjuvants used conventionally in compositions for dyeing the hair and as are defined above.

The composition which is finally applied to the keratin fibres may be in various forms, such as in the form of liquids, creams, gels or any other form which is suitable for dyeing keratin fibres, and in particular human hair.

Another subject of the invention is a multi-compartment device for dyeing or dyeing "kit" or any other multi-compartment packaging system a first compartment of which contains the dye composition as defined above and a second compartment of which contains the oxidizing composition as defined above. These devices may be equipped with a means which makes it possible to deliver the desired mixture onto the hair, such as the devices described in patent FR-2,586,913 in the name of L'Oréal, the disclosure of which is specifically incorporated by reference herein.

The examples which follow are intended to illustrate the invention without, however, limiting the scope thereof.

EXAMPLES

Examples 1 and 2

The following dye compositions in accordance with the invention were prepared (contents in grams):

| EXAMPLE | 1 | 2 |
|---|---|---|
| 2-n-Propyl-para-phenylenediamine dihydrochloride (oxidation base) | 1.1 | 1.1 |
| 2-Amino-4-N-(β-hydroxyethyl)amino-1-methoxybenzene dihydrochloride (coupler) | 1.275 | — |

-continued

| | | |
|---|---|---|
| 2,4-Diamino-1,5-di(β-hydroxyethyloxy)benzene dihydrochloride (coupler) | — | 1.5 |
| Common dye support (*) | (*) | (*) |
| Water qs | 100 g | 100 g |

(*) common dye support:

| | |
|---|---|
| Oleyl alcohol polyglycerolated with 2 mol of glycerol | 4.0 g |
| Oleyl alcohol polyglycerolated with 4 mol of glycerol, containing 78% of active material (AM) | 5.69 g AM |
| Oleic acid | 3.0 g |
| Oleylamine containing 2 mol of ethylene oxide, sold under the trade name Ethomeen O12 by the company Akzo | 7.0 g |
| Diethylaminopropyl laurylamino-succinamate, sodium salt, containing 55% AM | 3.0 g AM |
| Oleyl alcohol | 5.0 g |
| Oleic acid diethanolamide | 12.0 g |
| Propylene glycol | 3.5 g |
| Ethyl alcohol | 7.0 g |
| Dipropylene glycol | 0.5 g |
| Propylene glycol monomethyl ether | 9.0 g |
| Sodium metabisulphite in aqueous solution, containing 35% AM | 0.455 g AM |
| Ammonium acetate | 0.8 g |
| Antioxidant, sequestering agent | qs |
| Fragrance, preserving agent | qs |
| Aqueous ammonia containing 20% $NH_3$ | 10.0 g |

Each dye composition was mixed, at the time of use, with an equal amount of an oxidizing composition of 20-volumes aqueous hydrogen peroxide solution (6% by weight) and having a pH of about 3.

Each resulting mixture had a pH of about 10.2 and was applied for 30 minutes to locks of natural or permanent-waved grey hair containing 90% white hairs. The locks of hair were then rinsed, washed with a standard shampoo and then dried.

The locks of hair were dyed in the shades featured in the table below:

| EXAMPLE | SHADE ON NATURAL HAIR | SHADE ON PERMANENT-WAVED HAIR |
|---|---|---|
| 1 | blue | midnight blue |
| 2 | blue | midnight blue |

Comparative Examples 3 to 5

The following dye compositions were prepared (contents in grams):

| EXAMPLE | 3() | 4(*) | 5(***) |
|---|---|---|---|
| 2-n-Propyl-para-phenylenediamine dihydrochloride (oxidation base) | 0.669 | — | — |
| Para-phenylenediamine (oxidation base) | — | 0.324 | — |
| Para-toluylenediamine (oxidation base) | — | — | 0.366 |
| 2,4-Diamino-1-(β-hydroxyethyloxy)benzene dihydrochloride (coupler) | 0.723 | 0.723 | 0.723 |

-continued

| EXAMPLE | 3() | 4(*) | 5(***) |
|---|---|---|---|
| Common dye support(*) | (*) | (*) | (*) |
| Water qs | 100 g | 100 g | 100 g |

(*)this is identical to that of Examples 1 and 2
(**)example forming part of the invention
(***)examples not forming part of the invention Each dye composition comprises the same molar amount of oxidation base, namely $3 \times 10^{-3}$ mol.

Each dye composition was mixed, at the time of use, with an equal amount of 20-volumes aqueous hydrogen peroxide solution (6% by weight) and having a pH of about 3.

Each resulting mixture had a pH of about 10.2 and was applied for 30 minutes to locks of permanent-waved grey hair containing 90% white hairs. The locks of hair were then rinsed, washed with a standard shampoo and then dried.

The colour of the locks was then evaluated in the Munsell system, using a Minolta CM 2002 calorimeter.

According to the Munsell notation, a colour is defined by the expression HV/C in which the three parameters respectively denote the shade or Hue (H), the intensity or Value (V) and the purity or Chromaticity (C), the oblique line in this expression simply being a convention and not indicating a ratio.

The locks of hair thus dyed were then subjected to a test of resistance to washing (Ahiba-Texomat machine).

To do this, the locks of hair were placed in a basket which was immersed in a solution of a standard shampoo. The basket was subjected to an up-and-down motion of variable frequency as well as to a rotational motion, which reproduced the action of manual rubbing, thereby causing the formation of foam.

After a test time of 3 minutes, the locks were removed and then rinsed and dried. The dyed locks were subjected to 6 consecutive shampooing tests.

The colour of the locks was then evaluated again in the Munsell system using a Minolta CM 2002 calorimeter.

The difference between the colour of the lock before and after shampooing was calculated by applying the Nickerson formula: $\Delta E = 0.4 \text{ Co}\Delta H + 6\Delta V + 3\Delta C$, as described, for example, in "Couleur, Industrie et Technique"; pages 14–17; vol. No. 5; 1978.

In this formula, $\Delta E$ represents the difference in colour between two locks, $\Delta H$, $\Delta V$ and $\Delta C$ represent the variation in absolute value of the parameters H, V and C, and Co represents the purity of the lock relative to which it is desired to evaluate the colour difference.

The results are given in the table below:

| EXAMPLE | Colour of the hair before the shampooings | Colour of the hair after the shampooings | Degradation of the colour | | | |
|---|---|---|---|---|---|---|
| | | | $\Delta H$ | $\Delta V$ | $\Delta C$ | $\Delta E$ |
| 3 | 7.3 PB 2.0/2.0 | 6.7 PB 2.8/0.9 | 0.6 | 0.8 | 1.1 | 8.6 |
| 4 | 9.2 PB 1.9/0.8 | 5.3 RP 3.2/0.5 | 16.1 | 1.3 | 0.3 | 13.9 |
| 5 | 8.4 PB 1.9/1.5 | 9.6 PB 3.1/2.9 | 1.2 | 1.2 | 1.4 | 12.1 |

These results show that the composition of Example 3 in accordance with the invention, that is to say the one comprising 2-n-propyl-para-phenylenediamine and a meta-phenylenediamine of formula (I) in accordance with the invention, leads to a coloration which is of much better staying power with regard to shampooing than the colorations obtained with the compositions of Examples 4 and 5 which do not form part of the invention since they contain, respectively, para-phenylenediamine or para-toluylenediamine which are oxidation bases that do not form part of the invention.

What is claimed is:

1. A composition for the oxidation dyeing of keratin fibres comprising, in a medium which is suitable for dyeing:
   at least one oxidation base selected from 2-n-propyl-para-phenylenediamine and acid addition salts thereof,
   at least one coupler selected from meta-phenylenediamines of formula (I) below and acid addition salts thereof:

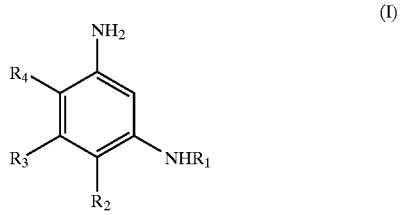

wherein:
   $R_1$ represents a hydrogen atom or a $C_1$–$C_4$ alkyl, $C_1$–$C_4$ monohydroxyalkyl or $C_2$–$C_4$ polyhydroxyalkyl radical;
   $R_2$ and $R_3$, which may be identical or different, represent a hydrogen atom or a $C_1$–$C_4$ alkyl, $C_1$–$C_4$ monohydroxyalkoxy or $C_2$–$C_4$ polyhydroxyalkoxy radical;
   $R_4$ represents a hydrogen atom or a $C_1$–$C_4$ alkoxy, $C_1$–$C_4$ aminoalkoxy, $C_1$–$C_4$ monohydroxyalkoxy or $C_2$–$C_4$ polyhydroxyalkoxy radical or a 2,4-diaminophenoxyalkyl radical.

2. A composition according to claim 1 wherein said keratin fibres are human keratin fibres.

3. A composition according to claim 2 wherein said human keratin fibres are hair.

4. A composition according to claim 1 wherein said meta-phenylenediamines of formula (I) are selected from meta-phenylenediamine, 3,5-diamino-1-ethyl-2-methoxybenzene, 3,5-diamino-2-methoxy-1-methylbenzene, 2,4-diamino-1-ethoxybenzene, 1,3-bis(2,4-diaminophenoxy)propane, bis(2,4-diaminophenoxy)methane, 1-(β-aminoethyloxy)-2,4-diaminobenzene, 2-amino-1-(β-hydroxyethyloxy)-4-methylaminobenzene, 2,4-diamino-1-ethoxy-5-methylbenzene, 2,4-diamino-5-(β-hydroxyethyloxy)-1-methylbenzene, 2,4-diamino-1-(β,γ-dihydroxypropyloxy)benzene, 2,4-diamino-1-(β-hydroxyethyloxy)benzene and 2-amino-4-N-(β-hydroxyethyl)amino-1-methoxybenzene, and acid addition salts thereof.

5. A composition according to claim 1 wherein said acid addition salts are selected from hydrochlorides, hydrobromides, sulphates and tartrates.

6. A composition according to claim 1 wherein said at least one oxidation base represents from 0.0005 to 10% by weight relative to the total weight of the dye composition.

7. A composition according to claim 6 wherein said at least one oxidation base represents from 0.05 to 7% by weight relative to the total weight of the dye composition.

8. A composition according to claim 1 wherein said at least one coupler represents from 0.0001 to 5% by weight relative to the total weight of the dye composition.

9. A composition according to claim 8 wherein said at least one coupler represents from 0.005 to 3% by weight relative to the total weight of the dye composition.

10. A composition according to claim 1 wherein said medium which is suitable for dyeing comprises water.

11. A composition according to claim 10 wherein said medium comprises a mixture of water and at least one organic solvent selected from $C_1$–$C_4$ lower alkanols, glycerol, glycols, glycol ethers, and aromatic alcohols.

12. A composition according to claim 1 wherein said composition has a pH ranging from 5 to 12.

13. A composition according to claim 1 wherein said composition further contains at least one additional ingredient selected from couplers and oxidation bases.

14. A process for dyeing keratin fibres comprising the steps of applying to said fibres a composition according to claim 1 and developing a color at an acidic, neutral or alkaline pH by with an oxidizing agent.

15. A process according to claim 14 wherein said oxidizing agent is combined with said composition and immediately thereafter said composition and said oxidizing agent are applied to said fibres.

16. A process according to claim 14 wherein said oxidizing agent is combined with said composition after said composition is applied to said fibres.

17. A process according to claim 14 wherein said oxidizing agent is applied to said fibres and thereafter said composition is applied to said fibres.

18. A process according to claim 14 wherein said oxidizing agent and said composition are separately and simultaneously applied to said fibres.

19. A process according to claim 14 wherein said keratin fibres are human keratin fibres.

20. A process according to claim 19 wherein said human keratin fibres are hair.

21. A process according to claim 14 wherein said oxidizing agent is selected from hydrogen peroxide, urea peroxide, alkali metal bromates and persalts.

22. A process according to claim 21 wherein said persalts are selected from perborates and persulphates.

23. A multi-compartment device for dyeing or multi-compartment dyeing kit comprising a first compartment containing a dye composition according to claim 1 and a second compartment containing an oxidizing agent.

* * * * *